United States Patent [19]

Sarup et al.

[11] Patent Number: 5,118,868
[45] Date of Patent: Jun. 2, 1992

[54] CATALYST FOR PREPARING ALDEHYDE

[75] Inventors: Bent Sarup, Frederiksberg; Poul E. H. Nielsen, Fredensborg; Viggo L. Hansen, Bronshoj; Keld Johansen, Frederikssund, all of Denmark

[73] Assignee: Haldor Topsoe A/S, Denmark

[21] Appl. No.: 596,677

[22] Filed: Oct. 12, 1990

[30] Foreign Application Priority Data

Oct. 16, 1989 [DK] Denmark .................. 5319/89
Dec. 4, 1989 [DK] Denmark .................. 6093/89

[51] Int. Cl.⁵ .................................... C07C 45/29
[52] U.S. Cl. ........................... 568/474; 568/471; 568/472
[58] Field of Search ................. 568/474, 471, 472

[56] References Cited

U.S. PATENT DOCUMENTS 1,693,092  1/1973  Cavalli et al. ............ 568/474
2,504,402  4/1950  Field ....................... 260/603
4,306,089 12/1981  Webster et al. ........... 568/472

FOREIGN PATENT DOCUMENTS 315047  10/1988  European Pat. Off. .
1693092  1/1973  Fed. Rep. of Germany ...... 568/474
2630928  1/1978  Fed. Rep. of Germany ...... 568/474
3213413 10/1981  Fed. Rep. of Germany ...... 568/472
1463174  2/1977  United Kingdom ............. 568/474

Primary Examiner—Werren B. Lone
Attorney, Agent, or Firm—Ostrolenk, Faber, Gerb & Soffen

[57] ABSTRACT

A catalyst for the partial oxidation of an alcohol to a corresponding aldehyde. The catalyst includes a monolithic structured inert carrier and an active catalytic mixture of oxides of molybdenum and either chromium, vanadium, aluminum, iron, tungsten, manganese or mixtures thereof in a molar ratio of the molybdenum oxide to the other oxide or oxides of between 1 and 5. The catalyst has a reduced pressure drop compared to a particulate catalyst bed.

8 Claims, No Drawings

CATALYST FOR PREPARING ALDEHYDE

The present invention relates to the preparation of aldehyde. In particular, the present invention is concerned with a monolithic structured catalyst for use in the preparation of aldehydes.

A widely employed process for the production of formaldehyde on industrial scale is oxidation of methanol to formaldehyde. This process is usually carried out by passing methanol-containing gas over particle shaped oxidation catalyst.

Due to the heat developed during the oxidation of methanol the process is ordinarily carried out in a wall cooled, tubular reactor.

An important feature of this process is the performance of the catalyst and reactor, which is measured as the optimum yield of formaldehyde calculated on the mole ratio of formaldehyde obtained and methanol fed to the reactor.

Catalysts, providing a high selectivity during the oxidation of methanol to formaldehyde, are the known unsupported catalysts based on the oxides of iron and molybdenum, such as $Fe_2(MoO_4)_3$—$MoO_3$ as disclosed in U.S. Pat. No. 1,913,405 and chromium oxide stabilized unsupported ferric oxide-molybdenum oxide catalysts as mentioned in U.S. Pat. No. 3,194,771.

It is well known that the selectivity of the particle shaped oxidation catalysts decreases with increasing conversion to aldehyde resulting in a barrier for the optimum yield obtainable. Thus, at conversion levels of methanol at about 98-99% the selectivity decreases with increasing methanol conversion giving a maximum obtainable formaldehyde yield of between 92-93%. To improve the selectivity the catalyst is used as small particles, possibly supported on a carrier as suggested in U.S. Pat. No. 4,181,629; U.S. Pat. No. 4,471,141; and SU 1,028,353, which can be used in fluidized beds.

A serious drawback of the known particle shaped oxidation catalysts is, however, pressure drop limitations caused by use of small particles in traditional fixed bed reactors. Small supported catalyst particles have, so far, not been successfully used in fluidized bed reactors on industrial scale apparently due to the lack of sufficient attrition resistance of the catalyst particles.

It has now been found that Mo based catalysts supported on a monolithic carrier provide an oxidation catalyst with an improved performance during conversion of alcohols to corresponding aldehydes, by reduced pressure drop compared to a catalyst bed of particulate catalyst. It has further been observed that when the monolithic supported catalyst is used in an adiabatic reactor after a wall cooled reactor, the formation of by-products such as formic acid and dimethylether is reduced.

Pursuant to these findings and observations, an object of the present invention is to provide an improved catalyst for the conversion of alcohols to aldehydes, which catalyst comprises as active catalytic material mixed oxides of molybdenum and a further component M, wherein M is selected from the group of chromium, vanadium, aluminum, iron, tungsten, manganese and mixtures thereof in a molar ratio Mo: M of between 1 and 5, the improvement of which comprises a monolithic structured inert carrier for the catalytic active material.

In a preferred embodiment of the invention the monolithic structured carrier is reinforced by a binder applied thereon.

The amount of the active material on the monolithic carrier may vary from 1 to 90% by weight with respect to the total amount of active material, carrier and binder. Preferably, the active material is loaded on the carrier in an amount of 80-90% by weight calculated on the total amount of active material, carrier and binder.

A further object of the invention is the use of the improved catalyst for the oxidation of alcohols to corresponding aldehydes, preferably methanol to formaldehyde.

The improved catalyst of the present invention may be prepared by a process, comprising the steps of corrugating sheets of fibrous inert carrier material;

coating the corrugated sheets with a slurry, containing active catalytic material and optionally a binder; and drying; and calcining the corrugated and coated sheets.

Suitable fibrous carrier material for use in the invention is any heat-resistant material, which is inert with respect to the conversion of alcohols to aldehydes, such as fibrous sheets of silica, with an average fibre diameter of between 50 and 250 micrometer and an average fibre length of between 2 and 30 mm.

The fibrous sheets are corrugated in a conventional corrugating machine and formed into a monolithic structured body by rolling up a single corrugated sheet to a cylindrical body having straight channels through the body. Preferably the monolithic structured body is formed into a cross-corrugated structure by piling up a number of the corrugated sheets to parallel layers with different orientation of the corrugation among the layers.

In either case the monolithic body is loaded by immersion or washcoating with an aqueous slurry containing the catalytic active material and optionally the binder for stabilizing the structure.

The catalytic active material for use in the invention may be obtained by coprecipitation from an aqueous solution containing soluble compounds of molybdenum and the component M in a molar ratio of Mo:M between 1 and 5, preferably 1.5 and 3. The precipitate is dried and calcined to convert the constituents to their active oxidic form. Alternatively, the oxides of molybdenum and of the component M, may be grounded together and calcined. In any case, the catalytic active material thus obtained has a specific surface area of 1 to 7 $m^2/g$.

Suitable binders for reinforcing the monolithic structured carrier are any of the known binder materials, which are inert with respect to the oxidation of the alcohol, such as silica, titania and the like.

The thus prepared monolithic structured catalyst may be used in adiabatic and cooled reactors for the partial oxidation of an alcohol containing feed gas to a corresponding aldehyde.

The partial oxidation of e.g. methanol to formaldehyde may further be obtained in a number of adiabatic catalyst beds containing the monolithic catalyst according to the invention and connected in series with cooling and methanol injection between the beds.

Having thus described the general aspects of the invention the following Examples are given to illustrate more detailed preferred embodiments thereof.

EXAMPLE 1

160 ml of an aqueous solution containing 130 g Fe(NO$_3$)$_3$.9H$_2$O and 43 g Cr(NO$_3$)$_3$.9H$_2$O and 140 ml of an aqueous solution containing 96 ml 25 wt % NH$_4$OH and 131 g MoO$_3$ are mixed in an agitated vessel. The combined solution is evaporated to dryness and subsequently thermally decomposed at 250°–300° C. to remove NH$_4$NO$_3$. The remaining solid is calcined at 525° C. for 1 hour and finally grounded in a ball mill.

EXAMPLE 2

1377 ml of an aqueous solution of 772 g Al(NO$_3$)$_3$.9H$_2$O and 768 g Cr(NO$_3$)$_3$.9H$_2$O are mixed with 2150 ml of an aqueous solution containing 869 ml 25% NH$_3$ and 873 g MoO$_3$.

The combined solution is then filtered and the obtained solid washed with destilled water to remove NH$_4$NO$_3$.

EXAMPLE 3

This Example illustrates the preparation of a monolithic structured iron-chromium-molybdate catalyst with straight channels through the monolith according to an embodiment of the invention, for use in the partial oxidation of methanol to formaldehyde.

A sheet of silica rich heat-resistant paper of 0.25 mm in thickness and consisting of silica fibres with a diameter of about 250 micrometer and a length of about 2 mm is corrugated by a conventional corrugating-machine, giving a corrugated sheet with a corrugation height of about 2.5 mm. The corrugated sheet is then rolled up to a straight channel monolith with an outer diameter of 50 mm and a height of 50 mm.

A slurry for immersing therein the so formed monolith is prepared by mixing 1200 g of the catalytic active material as prepared in Example 1 and 845 g ammonia stabilized SiO$_2$-binder, supplied by Monsanto Co., Ruabon, United Kingdom under the tradename Syton T40, and 250 g demineralized water.

The slurry is ball milled at ambient temperature for 24 hours, after which the monolith is immersed repeatedly in the slurry and dried at ambient temperature, until a final load of catalytic active material and binder of 90% by weight calculated on the total amount of active material, binder and monolith. The monolithic catalyst is then dried at 20° C. for 24 hours and calcined at 450° C. for 2 hours.

EXAMPLE 4

Preparation of a straight channel monolithic aluminum-molybdate catalyst according to the invention.

A slurry for immersing therein the so formed monolith is prepared by mixing 360 g of the catalytic active material as prepared in Example 2 and 90 g ammonia stabilized SiO$_2$-binder, supplied by Monsanto Co., Ruabon, United Kingdom under the tradename Syton T40, and 818 g demineralized water.

The slurry is ball milled at ambient temperature for 24 hours, after which the monolith is immersed in the slurry, then dried at ambient temperature and calcined at 420° C. for 30 min. This procedure was repeated twice giving a final load of catalytic active material and binder of 77% by weight calculated on the total amount of active material, binder and monolith. The monolithic catalyst was finally calcined at 600° C. for 90 min.

EXAMPLE 5

This Example illustrates the preparation of a cross corrugated monolithic iron-chromium-molybdate catalyst according to the invention for use in the oxidation of methanol to formaldehyde.

A number of corrugated sheets, as described in Example 3, each provided with a liner made from the same material as the corrugated sheets, are piled up as parallel layers, wherein the corrugation among the layers is at a right angle, giving a cross corrugated monolith.

The so formed monolith is washcoated once by the slurry prepared in Example 3 containing the active material and the binder, then dried at 20° C. for 24 hours and calcinated at 450° C. for 2 hours.

Cylindrical bodies with a diameter of 21 mm and a height of 50 mm are cut out of the washcoated monolith.

The cylindrical bodies are washcoated again by the same slurry as mentioned above to an extent giving a final loading of active material thereon corresponding to 80% by weight calculated on the total amount of active material, binder and monolith.

The monolithic supported catalyst is finally dried and calcinated as described above.

EXAMPLE 6

This Example is carried out by a test of the cross corrugated monolithic catalyst as prepared in Example 5.

The cross corrugated monolithic catalyst in the form of a cylindrical body is fitted in a reactor tube with 21 mm i.d. and a height of 1200 mm. The loaded height of the monolith is 900 mm.

The wall of the reactor tube is kept at 271° C. by a cooling bath. Feed gas consisting of 6.5 vol % CH$_3$OH, 19.6 vol % O$_2$ and 74.2 vol % N$_2$ is passed through the reactor tube at a space velocity of 6000 h$^{-1}$.

By passage through the monolithic catalyst 99.3% of the methanol in the feed gas is converted to formaldehyde with a selectivity of 96.2%. The yield of formaldehyde is thus 95.6%.

EXAMPLE 7

Comparative performance of pellets and monolithic catalyst.

3 pieces of the monolithic catalyst of Example 5 having a diameter of 50 mm o.d. and a height of 50 mm with a total of 77 g active material are loaded in an adiabatic reactor having a diameter of 50 mm i.d.

The adiabatic reactor is connected to the outlet of the wall cooled reactor as described in Example 6 with the exception that the wall cooled reactor is loaded with 177 g crushed pellets of a conventional formaldehyde catalyst, supplied by Haldor Topsoe, Lyngby, Denmark, consisting of chromium promoted iron molybdate and molybdenum trioxide.

Feed gas, consisting of 8 vol % methanol, 9 vol % O$_2$ and nitrogen as balance, is passed through the wall cooled reactor at a velocity of 1900 Nl/h and a temperature of 271° C., whereby 95.5% of the methanol is converted. The reacted gas leaving the cooled reactor is further passed through the monolithic catalyst fitted in the adiabatic reactor.

The inlet temperature of the gas to the adiabatic reactor is varied to give exit temperatures at the outlet of this reactor of 300° C., 350° C. and 400° C. The results obtained by this experiment are shown below in Table 1. The pressure drop over the monolithic catalyst is 32 mm Hg.

In a further experiment the performance of the monolithic catalyst is compared to the conventional formaldehyde catalyst as described above. The monolithic catalyst loaded in the adiabatic reactor is now replaced by 77 g of the conventional catalyst, crushed to 1.0 to 1.7 mm particles.

At the same feed gas composition and under comparable conditions as in the first experiment a comparable methanol conversion rate and selectivity is obtained, except that the pressure drop over the conventional particulate catalyst has risen by about 20% compared to the monolithic catalyst to 40 mm Hg. The results of this experiment are listed below in Table 2.

TABLE 1

Performance of monolithic formaldehyde catalyst in adiabatic postconverter

| | Conversion % | Yield HCHO C% | CO C% | DME C% | CO$_2$ C% | HCOOH ppm*) | $\Delta$T exp. °C | $\Delta$p$^{S)}$ mmHg |
|---|---|---|---|---|---|---|---|---|
| Exit cooled reactor | 95.6 | 91.8 | 1.8 | 1.9 | 0.1 | 226 | — | — |
| Exit adiabatic reactor (°C) | | | | | | | | |
| 300° C | 99.1 | 94.2 | 2.5 | 1.8 | 0.6 | 150 | 23. | 32. |
| 350° C | 99.6 | 93.8 | 3.7 | 1.5 | 0.6 | 105 | 34. | 32. |
| 400° C | 99.5 | 91.9 | 5.3 | 1.5 | 0.9 | 95 | 52. | 34. |

*) Given as ppm (wt %) HCOOH in 37% wt % aqueous HCHO solution.
$^{S)}$ Including a pressure drop of about 25 mm Hg over the empty reactor system

TABLE 2

Performance of crushed (1-1.7 mm) conventional formaldehyde catalyst in adiabatic postconverter

| | Conversion % | Yield HCHO C% | CO C% | DME C% | CO$_2$ C% | HCOOH ppm*) | $\Delta$T exp. °C | $\Delta$p$^{S)}$ mmHg |
|---|---|---|---|---|---|---|---|---|
| Exit cooled reactor | 95.6 | 91.9 | 2.2 | 1.4 | 0.1 | 220 | — | — |
| Exit adiabatic reactor (°C) | | | | | | | | |
| 300° C | 99.3 | 94.4 | 2.7 | 1.6 | 0.5 | 152 | 18. | 40. |
| 350° C | 99.8 | 93.8 | 3.9 | 1.5 | 0.7 | 103 | 24. | 40. |
| 400° C | 99.0 | 93.0 | 4.3 | 1.3 | 1.3 | 94 | 35. | 45. |

*) Given as ppm (wt %) HCOOH in 37% wt % aqueous HCHO solution
$^{S)}$ Including a pressure drop of about 25 mm Hg over the empty reactor system

EXAMPLE 8

The straight channel monolithic catalyst of Example 4 is tested during the preparation of formaldehyde by partial oxidation of methanol in a similar procedure to that of Example 7. 3 pieces of the monolithic catalyst of Example 4 having a diameter of 50 mm o.d. and a height of 50 mm with a total of 72 g active catalytical material are now loaded in the adiabatic reactor having a diameter of 50 mm i.d.

At a space velocity of 6700 h$^{-1}$ and an exit temperature of 350° C. in the adiabatic reactor the conversion of methanol to formaldehyde increases from about 95% at the exit of the wall cooled temperature to 99.3% in the exit gas of the adiabatic reactor, giving a yield of formaldehyde of 92.5%. The pressure drop over the monolithic catalyst is measured to 33 mm Hg including a pressure drop of about 25 mm Hg over the empty reactor system.

EXAMPLE 9

In this Example a straight channel monolithic catalyst, as described in Example 3, is tested in a simulated process for the partial oxidation of methanol to formaldehyde. The partial oxidation of methanol is computed to be carried out in 4 adiabatic catalyst beds connected in series with cooling and methanol injection between the beds. 12,500 Nm$^3$/h feed gas containing 9.1 vol % methanol, 10 vol % O$_2$ together with nitrogen as balance and mixed with 336 Nm$^3$/h of methanol containing gas are passed at a total volumetric flow rate of 12,836 Nm$^3$/h to the first catalyst bed. To the effluent of each bed 1-2 further 336 Nm$^3$/h of the methanol containing gas are added before passing to the next bed. To the effluent of bed 3 247 Nm$^3$/h of the methanol containing gas are added before it is passed to bed 4.

The temperature at the inlet of each catalyst bed is adjusted to about 250° C. by heat exchange The content of the active catalytic material is tabulated in Table 3 below together with the above mentioned process parameters. The overall conversion of methanol at the outlet of catalyst bed 4 is calculated to 98.4%.

TABLE 3

| Catalyst bed | Total flow (Nm$^3$/h) inlet | vol % Methanol in added gas | Temp. (C°) inlet | Catalytic active material (kg) |
|---|---|---|---|---|
| 1 | 12,836 | 2.6 | 250 | 410 |
| 2 | 13,338 | 2.5 | 249 | 480 |
| 3 | 13,837 | 2.6 | 251 | 480 |
| 4 | 14,229 | 2.2 | 248 | 780 |

At a linear velocity of 0.27 Nm/s a pressure drop of 47 mm Hg over the monolithic catalyst is calculated, when using 8.5 m$^3$ of the catalyst with a bulk density of 0.27 g/cm$^3$.

To reach 98.4% methanol conversion, as it is the case in the above computation model, a total of 2.2 m$^3$ of the crushed conventional formaldehyde catalyst with a particle diameter of 1.5 mm and a bulk density of 1 g/cm³ would be needed. giving a pressure drop over the catalyst of 375 mm Hg at an equivalent linear velocity as mentioned above.

Having thus described the invention in detail with respect to preferred embodiments thereof, it is to be understood that various changes, which will be readily apparent to those skilled in the art are contemplated as within the scope of the present invention, which is limited only by the claims which follow.

We claim:

1. A method for the partial oxidation of a lower alcohol in an alcohol-containing gas to a corresponding lower aldehyde using oxygen as an oxidizing agent, the process including the step of catalyzing the oxidation using a catalyst comprising: a) mixed oxides of molybdenum and a further component M, wherein M is selected from the oxides of chromium, vanadium, aluminum, iron, tungsten, manganese and mixtures thereof, in a molar ratio Mo:M of between 1 and 5; and b) a monolithic structured inert carrier for the mixed oxides.

2. The method of claim 1, wherein the alcohol containing gas comprises methanol.

3. The method of claim 2, wherein methanol constitutes from 3 to 10% by volume in the alcohol containing gas.

4. The method of claim 1, wherein the partial oxidation is carried out in a wall cooled reactor.

5. The method of claim 1, wherein the partial oxidation is carried out in an adiabatic reactor.

6. The method of claim 1, wherein the partial oxidation is carried out in a wall cooled reactor and a post-connected adiabatic reactor.

7. The method of claim 1, wherein the partial oxidation is carried out in at least two adiabatic reactors connected in series.

8. The method of claim 7, wherein alcohol containing gas further is added between the reactors.

* * * * *